(12) United States Patent
Higuchi et al.

(10) Patent No.: US 11,898,128 B2
(45) Date of Patent: Feb. 13, 2024

(54) CULTURE APPARATUS AND CULTURE METHOD

(71) Applicant: CANON KABUSHIKI KAISHA, Tokyo (JP)

(72) Inventors: Akira Higuchi, Toyonaka (JP); Hiroyuki Naito, Toyonaka (JP); Itsuro Motegi, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 110 days.

(21) Appl. No.: 16/622,141

(22) PCT Filed: Aug. 1, 2018

(86) PCT No.: PCT/IB2018/055759
§ 371 (c)(1),
(2) Date: Dec. 12, 2019

(87) PCT Pub. No.: WO2018/229740
PCT Pub. Date: Dec. 20, 2018

(65) Prior Publication Data
US 2020/0131460 A1  Apr. 30, 2020

(30) Foreign Application Priority Data
Jun. 15, 2017 (JP) .................. 2017-117882

(51) Int. Cl.
*C12M 1/00* (2006.01)
*C12M 1/04* (2006.01)
(Continued)

(52) U.S. Cl.
CPC ............ *C12M 23/14* (2013.01); *C12M 23/24* (2013.01); *C12M 23/26* (2013.01); *C12M 27/16* (2013.01); *C12M 41/32* (2013.01)

(58) Field of Classification Search
None
See application file for complete search history.

(56) References Cited

U.S. PATENT DOCUMENTS 4,702,610 A * 10/1987 Reynolds, Jr. ........ B01F 35/422
366/208
5,057,429 A * 10/1991 Watanabe .............. C12M 25/02
435/297.1
(Continued)

FOREIGN PATENT DOCUMENTS

JP  H03-007575  1/1991
JP  H05-284961  11/1993
(Continued)

OTHER PUBLICATIONS

International Preliminary Report on Patentability issued for PCT/IB2018/055759, dated Dec. 26, 2019, 10 pages.
(Continued)

*Primary Examiner* — Michael L Hobbs
*Assistant Examiner* — Nathan G Esperon
(74) *Attorney, Agent, or Firm* — Venable LLP

(57) ABSTRACT

A culture apparatus includes a culture vessel including an internal space containing a culture solution in which a culture target is suspended, a gas supply apparatus supplying a single gas or a mixed gas to the internal space of the culture vessel, and an agitation apparatus agitating the culture solution by changing position and posture of the culture vessel. The agitation apparatus changes the position and posture of the culture vessel to circulate the culture solution in the internal space of the culture vessel so that a bottom surface of the internal space of the culture vessel is partially revealed and that the revealed portion transitions in a circulating direction R.

8 Claims, 10 Drawing Sheets

(51) Int. Cl.
*C12M 1/34* (2006.01)
*C12M 3/06* (2006.01)

(56) References Cited

U.S. PATENT DOCUMENTS

| | | | | |
|---|---|---|---|---|
| 5,921,676 | A * | 7/1999 | Reynolds | C12M 27/16 366/208 |
| 7,510,866 | B2 * | 3/2009 | Choi | C12M 23/46 73/796 |
| 2003/0064513 | A1 * | 4/2003 | Uemura | C12M 27/10 435/366 |
| 2005/0176140 | A1 * | 8/2005 | Benedict | C12M 27/02 435/366 |
| 2010/0144022 | A1 * | 6/2010 | Surapaneni | C12M 23/48 435/289.1 |
| 2011/0014689 | A1 * | 1/2011 | Gandlur | C12M 27/10 435/289.1 |
| 2013/0189767 | A1 * | 7/2013 | Cheng | C12M 41/12 435/295.1 |
| 2014/0011270 | A1 | 1/2014 | Chotteau et al. | |
| 2014/0178996 | A1 | 6/2014 | Shibuya et al. | |
| 2015/0024429 | A1 * | 1/2015 | Otter | B05D 1/40 435/40.51 |
| 2017/0073626 | A1 * | 3/2017 | Hata | B01F 31/23 |
| 2018/0016547 | A1 | 1/2018 | Hagihara et al. | |
| 2018/0305650 | A1 * | 10/2018 | Higuchi | C12M 27/16 |

FOREIGN PATENT DOCUMENTS

| | | |
|---|---|---|
| JP | H10-191960 | 7/1998 |
| JP | 2004-121168 | 4/2004 |
| JP | 2006-325410 | 12/2006 |
| JP | 2014-507959 | 4/2014 |
| JP | 2014-124139 | 7/2014 |
| WO | 2014/208358 | 12/2014 |
| WO | 2016/121773 | 8/2016 |
| WO | 2017/090752 | 6/2017 |
| WO | 2017/090757 | 6/2017 |

OTHER PUBLICATIONS

Office Action issued for the corresponding Japanese Patent Application No. 2017-117882, dated Feb. 2, 2021, 8 pages including machine translation.
International Search Report of PCT/IB2018/055759, dated Oct. 23, 2018, 2 pages.

* cited by examiner

CULTURE APPARATUS AND CULTURE METHOD

This application is a U.S. national stage of International Application No. PCT/IB2018/055759, filed Aug. 1, 2018, which claims the benefit of Japanese Application No. 2017-117882, filed Jun. 15, 2017.

BACKGROUND OF THE INVENTION

1. Field of the Invention

The present invention relates to a culture apparatus and a culture method for culturing cells etc. by using a culture solution.

2. Description of the Related Art

When culturing a culture target such as cells by using a culture solution, a conventionally known culture apparatus stirs the culture solution to dissolve gases such as oxygen and carbon dioxide (or a mixed gas thereof) necessary for culture in the culture solution.

For example, the culture apparatus described in Japanese Laid-Open Patent Publication No. 2014-124139 is configured to contain a culture solution in which cells are suspended in a cylindrical culture tank and to stir the culture solution with an agitation blade.

For example, the culture apparatus described in Japanese Unexamined Patent Application Publication (Translation of PCT Application) No. 2014-507959 is configured such that a culture bag (bioreactor bag) containing a culture solution having cells suspended therein is placed on a support and that the support is swung like a seesaw about an axis of oscillation extending in a horizontal direction to reciprocate the culture solution in one direction.

However, in the case of the culture apparatus described in Japanese Laid-Open Patent Publication No. 2014-124139, oxygen is taken and dissolved in the culture solution via a liquid surface. Therefore, an amount of dissolved oxygen in the culture solution may be insufficient in the vicinity of a bottom surface of a culture vessel far from the liquid surface. For a countermeasure, it is conceivable that a sparger is disposed on the bottom surface of the culture vessel to supply oxygen from the sparger into the culture solution. However, the cells are damaged due to impact caused by burst of oxygen bubbles generated from the sparger.

In the case of the culture apparatus described in Japanese Unexamined Patent Application Publication (Translation of PCT Application) No. 2014-507959, oxygen is taken and dissolved in the culture solution via a wave surface generated by the swing of the culture bag. In this culture apparatus, it is necessary to swing the culture bag more largely when the amount of dissolved oxygen is further increased in the culture solution. However, when the culture bag is largely swung, the culture solution strongly collides with an inner wall surface located on the lower side of the culture bag tilted by the swing. As a result, a local flow with a large shear stress is generated, so that the cells are damaged by the shear stress.

SUMMARY OF THE INVENTION

Therefore, a problem to be solved by the present invention is to dissolve, at the time of culture performed by agitating a culture solution in which a culture target such as cells is suspended, a gas necessary for the culture such as oxygen sufficiently and entirely in the culture solution while suppressing damages to the culture target.

To solve the technical problems, an aspect of the present invention provides a culture apparatus including:
a culture vessel including an internal space containing a culture solution in which a culture target is suspended;
a gas supply apparatus supplying a single gas or a mixed gas to the internal space of the culture vessel; and
an agitation apparatus agitating the culture solution by changing position and posture of the culture vessel, wherein
the agitation apparatus changes the position and posture of the culture vessel to circulate the culture solution in the internal space of the culture vessel so that a bottom surface of the internal space of the culture vessel is partially revealed and that the revealed portion transitions in a circulating direction.

Another aspect of the present invention provides
a culture method including:
supplying a single gas or a mixed gas to an internal space of a culture vessel containing a culture solution; and
agitating the culture solution by changing position and posture of the culture vessel to circulate the culture solution in the culture vessel so that a bottom surface of the internal space of the culture vessel is partially revealed and that the revealed portion transitions in a circulating direction.

According to the present invention, at the time of culture performed by agitating a culture solution in which a culture target such as cells is suspended, a gas necessary for the culture such as oxygen can sufficiently and entirely be dissolved in the culture solution while suppressing damages to the culture target in the culture solution.

DESCRIPTION OF THE PREFERRED EMBODIMENTS

Figure 1:
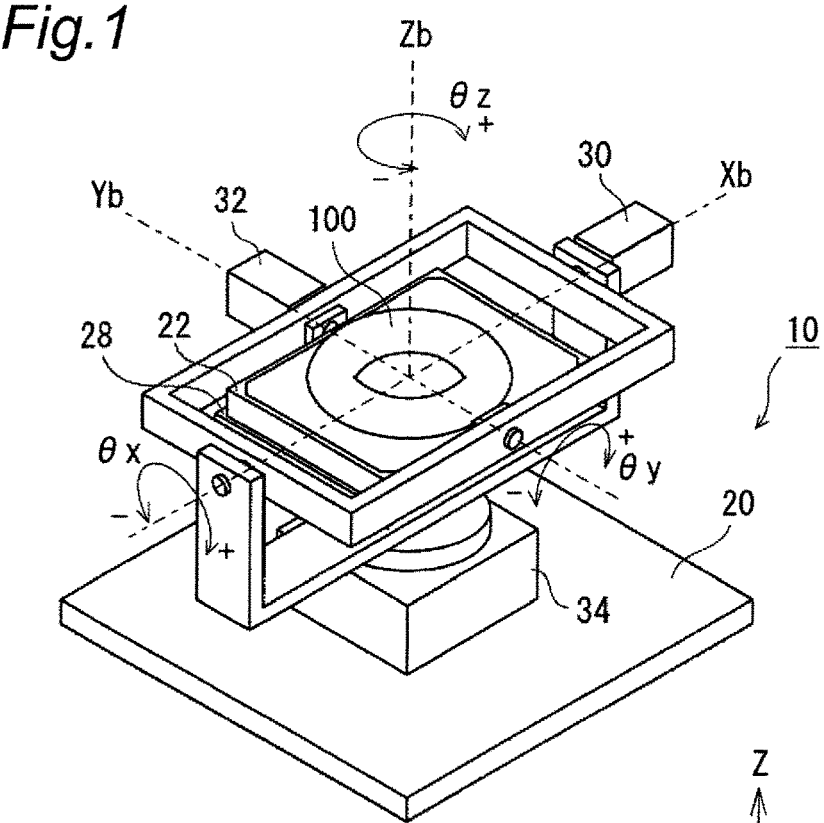
FIG. 1 is a schematic perspective view of a culture apparatus according to a first embodiment of the present invention.
Figure 1:
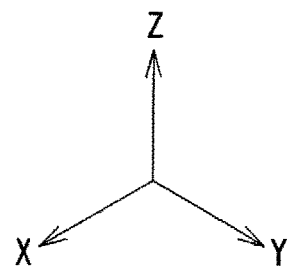

A culture apparatus according to an aspect of the present invention includes a culture vessel including an internal space containing a culture solution in which a culture target is suspended, a gas supply apparatus supplying a single gas or a mixed gas to the internal space of the culture vessel, and an agitation apparatus agitating the culture solution by changing position and posture of the culture vessel, and the agitation apparatus changes the position and posture of the culture vessel to circulate the culture solution in the internal space of the culture vessel so that a bottom surface of the internal space of the culture vessel is partially revealed and that the revealed portion transitions in a circulating direction.

According to this aspect, a gas necessary for culture such as oxygen can sufficiently and entirely be dissolved in the culture solution while suppressing damages to the culture target in the culture solution.

For example, the agitation apparatus is configured to tilt the culture vessel relative to a horizontal direction so that the bottom surface of the internal space of the culture vessel is partially revealed and to change a tilt direction of the culture vessel so that the revealed portion transitions in the circulating direction. As a result, the culture solution can be circulated in the internal space of the culture vessel so that the bottom surface of the internal space of the culture vessel is partially revealed and that the revealed portion transitions in a circulating direction.

For example, the agitation apparatus includes a stage holding the culture vessel, a first motor swinging the culture vessel at a first frequency about a first axis of oscillation extending in a horizontal direction, and a second motor swinging the culture vessel at a second frequency about a second axis of oscillation extending in a horizontal direction and orthogonal to the first axis of oscillation, and the first frequency and the second frequency are the same in wavelength and amplitude and different in phase by a quarter wavelength. As a result, the culture solution can be circulated in the internal space of the culture vessel so that the bottom surface of the internal space of the culture vessel is partially revealed and that the revealed portion transitions in a circulating direction.

For example, the agitation apparatus includes a stage holding the culture vessel, a rotary actuator including a rotating table rotating about a rotation center axis extending in a vertical direction, a oscillating head that supports the stage swingably about a first axis of oscillation extending in a horizontal direction and a second axis of oscillation extending in a horizontal direction and orthogonal to the first axis of oscillation and that includes a coupling shaft, a tilting mechanism including a oscillating head coupling part slidably disposed around the coupling shaft of the oscillating head, a base part attached to the rotating table of the rotary actuator, and a link arm including one end pivotally fixed to the oscillating head coupling part and the other end pivotally fixed to the base part, and a rotary actuator lifting/lowering mechanism lifting and lowering the rotary actuator in the vertical direction. As a result, the culture solution can be circulated in the internal space of the culture vessel so that the bottom surface of the internal space of the culture vessel is partially revealed and that the revealed portion transitions in a circulating direction.

The culture apparatus may include a dissolved oxygen measuring device measuring a concentration of dissolved oxygen in the culture solution and may control at least one of an area of the revealed portion on the bottom surface of the internal space of the culture vessel and a transition speed of the revealed portion based on the measured concentration of dissolved oxygen. As a result, an amount of dissolved gas in the culture solution can appropriately be adjusted.

The culture apparatus may include a pH measuring device measuring a pH value of the culture solution, and the culture apparatus may control at least one of the area of the revealed portion on the bottom surface of the internal space of the culture vessel and the transition speed of the revealed portion based on the measured pH value. As a result, the pH value of the culture solution can appropriately be controlled.

For example, the internal space of the culture vessel may be annular. This facilitates circulation of the culture solution in the internal space of the culture vessel.

For example, the culture vessel may be a flexible culture bag. This facilitates changes in position and posture of the culture vessel as compared to a heavy glass culture vessel, for example. Therefore, the culture solution in the internal space can more easily be stirred.

The culture target may be suspended cells or adherent cells acclimated to floating.

A culture method according to another aspect of the present invention includes: supplying a single gas or a mixed gas to an internal space of a culture vessel containing a culture solution; and agitating the culture solution by changing position and posture of the culture vessel to circulate the culture solution in the culture vessel so that a bottom surface of the internal space of the culture vessel is partially revealed and that the revealed portion transitions in a circulating direction.

According to this aspect, a gas necessary for culture such as oxygen can sufficiently and entirely be dissolved in the culture solution while suppressing damages to the culture target in the culture solution.

Embodiments of the present invention will now be described with reference to the drawings.

FIG. 1 schematically shows a culture apparatus according to an embodiment of the present invention. An X-Y-Z orthogonal coordinate system shown in the drawings is for facilitating understanding of the embodiments of the invention and does not limit the invention. X- and Y-axis directions are horizontal directions, and a Z-axis direction is a vertical direction.

As shown in FIG. 1, the culture apparatus 10 has a culture vessel 100 containing a culture solution in which a culture target is suspended, and a agitation apparatus 20 for agitating the culture solution in the culture vessel 100. The culture vessel 100 will first be described.

Figure 2:
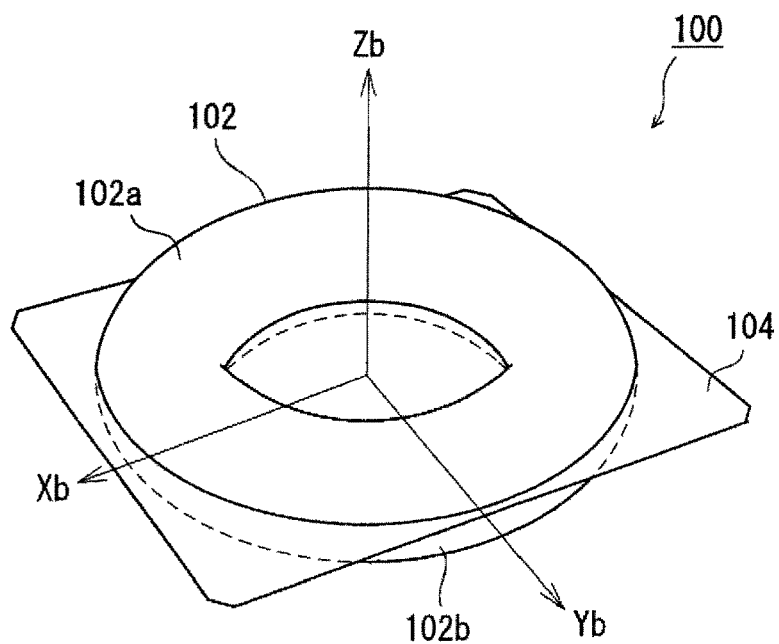
FIG. 2 is a schematic perspective view of a culture vessel.
Figure 3:
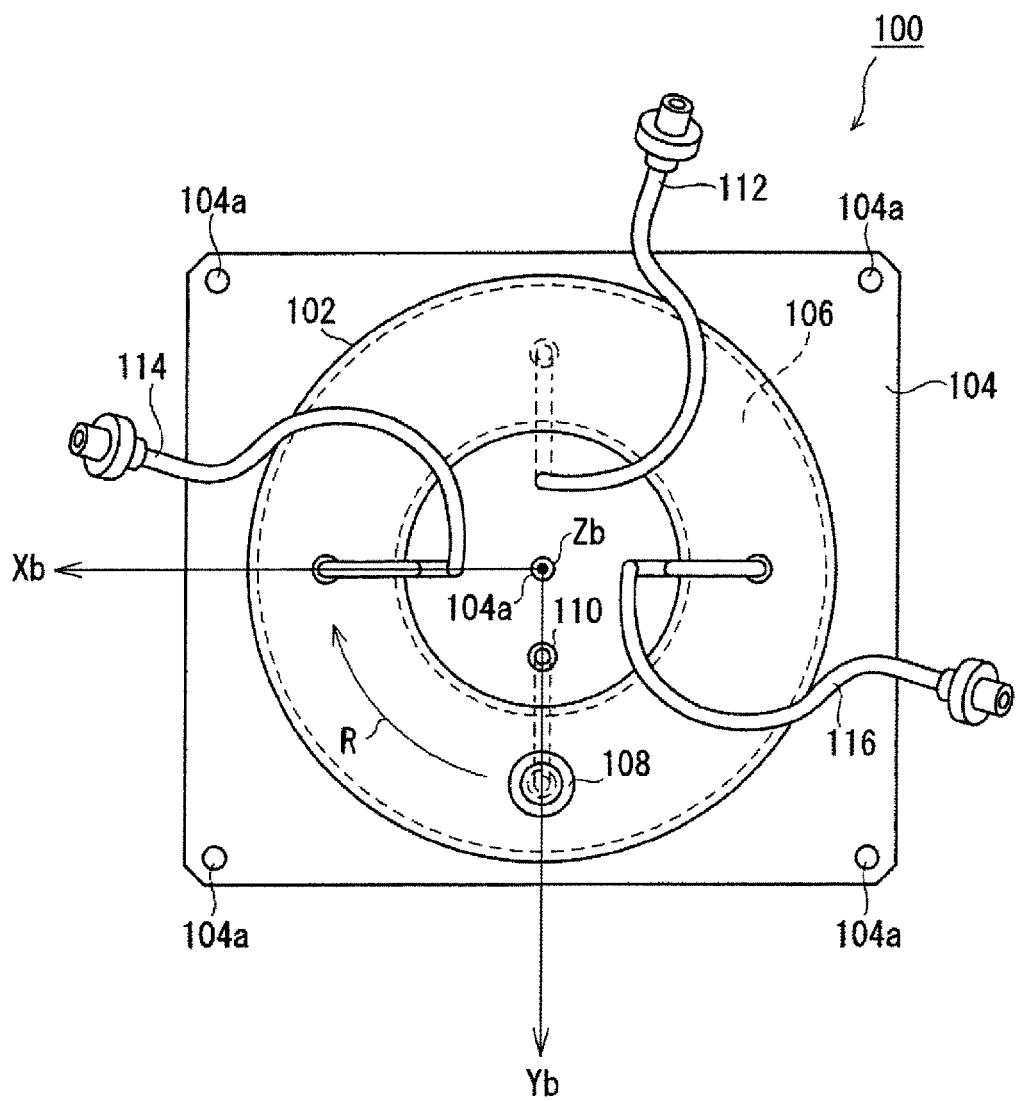
FIG. 3 is a top view of the culture vessel.

FIG. 2 is a schematic perspective view of the culture vessel 100. FIG. 3 is a top view of the culture vessel 100.

As shown in FIG. 2, in the case of this embodiment, the culture vessel 100 is a bag in which a culture target such as cells is cultured. The culture vessel will hereinafter be referred to as a culture bag. In the case of this embodiment, the culture bag 100 is made of a flexible material such as polyethylene or an elastomer material in consideration of single use so that the bag can be compressed at the time of disposal. Additionally, since the bag is lightweight as compared to a glass culture vessel, the bag is easily changed in position and posture, i.e., the culture solution in the culture bag 100 is easily stirred, as described later.

The culture bag 100 has a culture part 102 for containing and culturing a culture solution (cell suspension) in which a culture target such as cells is suspended at a constant concentration (number), and a sheet-shaped bracket part 104 holding the culture part 102. In the case of this embodiment, suspended cells required to be stirred are suspended as a culture target in the culture solution.

As shown in FIG. 3, the culture part 102 of the culture bag 100 includes an internal space 106 containing and culturing the culture solution. In the case of this embodiment, the internal space 106 is an endless circulating space allowing the culture solution to circulate and is a space having an annular shape, or specifically, a circular ring shape (or a donut shaped) having a circular vertical cross section) (see FIG. 5).

Several terms related to the annular internal space 106 are defined herein. First, the annular internal space 106 serving as the circulating space has a circulating direction defined as R. An axis orthogonal to a plane including the circulating direction R is defined as a third bag axis Zb. Axes included in the plane including the circulating direction R, orthogonal to the third bag axis Zb, and orthogonal to each other are defined as first and second bag axes Xb, Yb.

Furthermore, since the internal space 106 has a circular ring shape in the case of this embodiment, the third bag axis Zb is defined as a central axis passing through the center of the annular shape. The sheet-shaped bracket part 104 is developed along the first and second bag axes Xb, Yb.

The bracket part 104 holding the culture part 102 of the culture bag 100 functions as a bracket for attaching the culture bag 100 to the agitation apparatus 20. Therefore, in the case of this embodiment, the bracket part 104 of the culture bag 100 is provided with a plurality of through-holes 104a used when screwed to the agitation apparatus 20.

In the case of this embodiment, as shown in FIG. 2, the culture part 102 is disposed in the bracket part 104 to penetrate the bracket part 104. Specifically, the culture part 102 is divided by the bracket part 104 into an upper half 102a (a portion located on the upper side when attached to the culture apparatus 10) and a lower half 102b. However, the internal space 106 of the culture part 102 penetrates the bracket part 104.

In the case of this embodiment, the culture part 102 of the culture bag 100 is provided with a plurality of ports (hoses) 108, 110, 112, 114, and 116.

Each of the plurality of the ports 108, 110, 112, 114, and 116 communicates with the internal space 106 of the culture part 102.

The culture solution port 108 is a port used when the culture solution is supplied to the internal space 106 of the culture part 102 and the culture solution is recovered from the internal space 106. The culture solution port 108 is disposed in the upper half 102a of the culture part 102.

The sampling port 110 is used to acquire a sample of cells cultured in the internal space 106 of the culture part 102. A specified amount of the culture solution (cell suspension) can be collected from the culture bag 100 through this port 110. A progress of the culture can be known by observing the collected suspension with a microscope etc. For example, a degree of cell growth can be measured by counting the number of cells through a microscope. The sampling port 110 is a port including a luer lock connector with a valve, for example. The sampling port 110 extends from the lower half 102b of the culture part 102 and opens at the bracket part 104.

The first gas supply port 112 is a port used for supplying oxygen, carbon dioxide, or a mixed gas containing them necessary for culture into the internal space 106 of the culture part 102. For example, a mixed gas of carbon dioxide mixed with air, a mixed gas of nitrogen, oxygen, and carbon dioxide mixed at a predetermined mixing ratio is supplied via the first gas supply port 112 to the internal space 106. The first gas supply port 112 extends from the lower half 102b of the culture part 102.

The exhaust port 114 is a port used for exhausting the inside of the internal space 106 of the culture part 102 or adjusting the pressure inside the internal space 106 by the exhaust. The exhaust port 114 extends from the upper half 102a of the culture part 102.

The second gas supply port 116 is a port used for supplying oxygen, carbon dioxide, or a mixed gas containing them necessary for culture into the internal space 106 of the culture part 102 as with the first gas supply port 112. The second gas supply port 116 extends from the upper half 102a of the culture part 102. For example, the second gas supply port 116 is mainly used, and the first gas supply port 112 is accessorily used.

The positions of the plurality of ports 108, 110, 112, 114, and 116 disposed on the culture part 102 may be changed depending on a use of (a type of culture in) the culture bag 100. The first and second gas supply ports 112, 116 and the exhaust port 114 are provided with a filter for suppressing entry of foreign matter into the internal space 106 of the culture bag 100.

Figure 4:
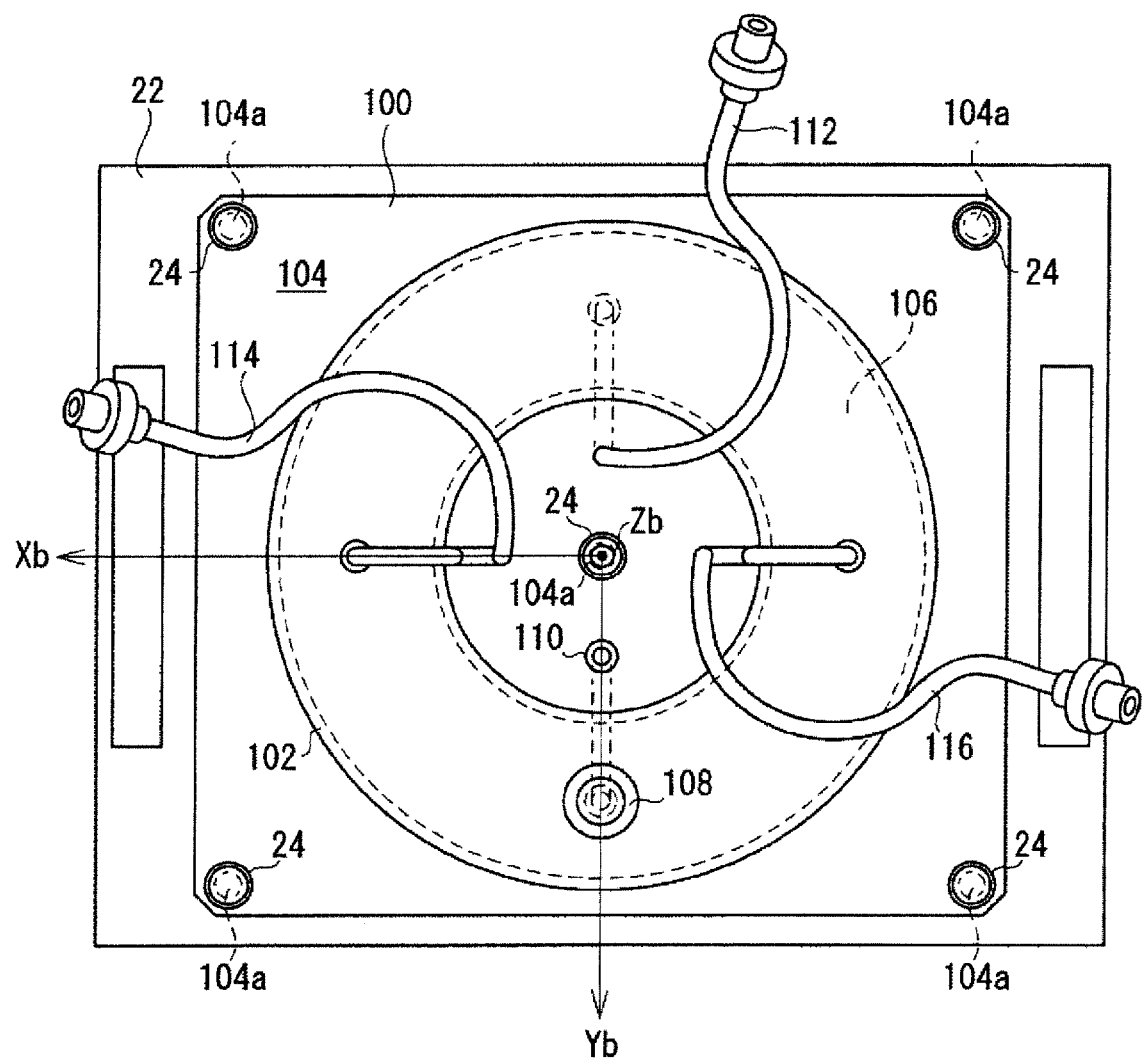
FIG. 4 is a top view of the culture vessel with a tray attached thereto.

In the case of this embodiment, the culture bag 100 fixed to the tray 22 as shown in FIG. 4 is attached to the agitation apparatus 20. The culture bag 100 is fixed to the tray 22 via a plurality of knurled screws 24 passing through a plurality of the through-holes 104a formed in the bracket part 104.

Figure 5:
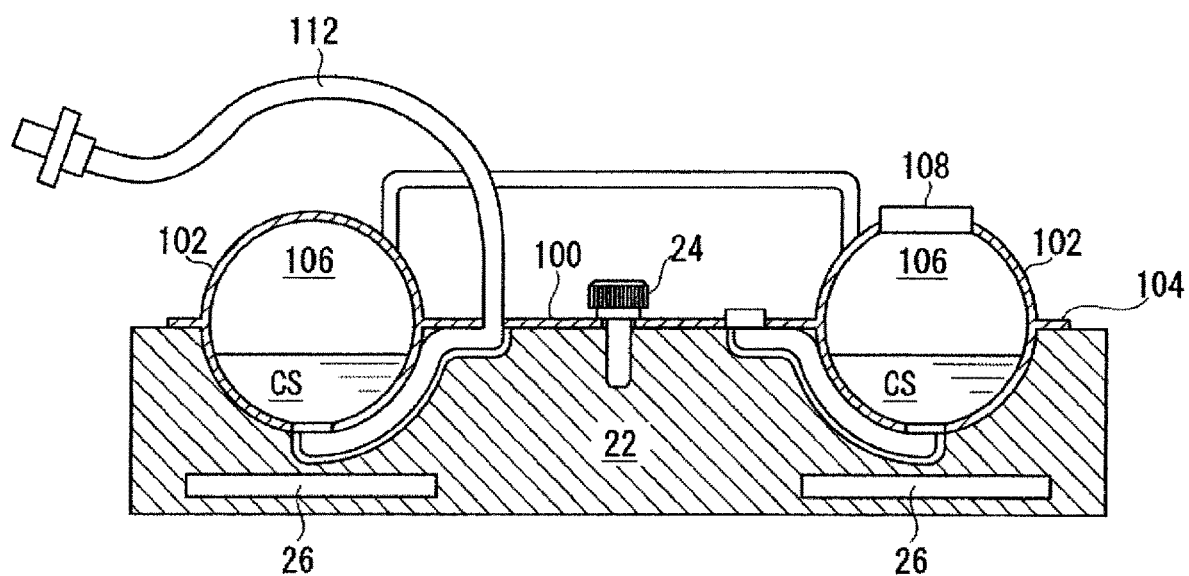
FIG. 5 is a cross-sectional view along an axis Yb shown in FIG. 4.

As shown in FIG. 5 showing a cross section along the axis Yb shown in FIG. 4, the tray 22 is provided with a heater 26 for adjusting the temperature in the internal space 106 of the culture part 102 of the culture bag 100.

As shown in FIG. 1, the agitation apparatus 20 includes a stage 28 on which the tray 22 is fixedly placed. The stage 28 holds the tray 22 such that the first bag axis Xb is parallel to the X axis, which is one horizontal axis, and that the second bag axis Yb is parallel to the Y axis, which is the other horizontal axis.

The agitation apparatus 20 also has a plurality of motors 30, 32, 34 for changing a posture of the stage 28, i.e., changing a posture of the culture bag 100 on the tray 22 placed on the stage 28.

The motor 30 is a swinging source swinging the culture bag 100 fixed to the stage 28 via the tray 22 about the first bag axis Xb (axis of oscillation) of the culture bag 100.

The motor 32 is a swinging source swinging the culture bag 100 fixed to the stage 28 via the tray 22 about the second bag axis Yb (axis of oscillation) of the culture bag 100.

The motor 34 is a swinging source swinging the culture bag 100 fixed to the stage 28 via the tray 22 about the third bag axis Zb of the culture bag 100.

The stage 28 is mounted on the agitation apparatus 20 such that the culture bag 100 placed on the stage 28 via the tray 22 can be swung about the first to third bag axes Xb, Yb, Zb.

The culture bag 100 fixed to the stage 28 via the tray 22 is changed in posture by these motors 30, 32, and 34. As a result, the culture solution in the internal space 106 of the culture part 102 of the culture bag 100 is stirred in the internal space 106.

Figure 6:
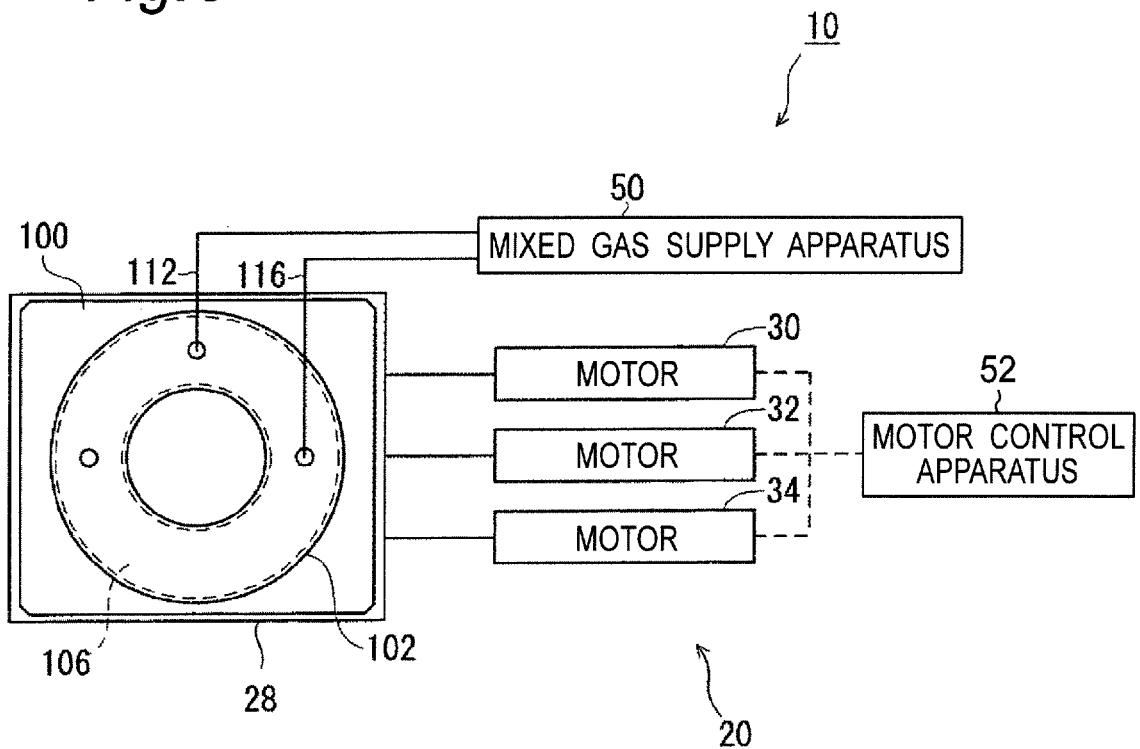
FIG. 6 is a block diagram showing a control system of the culture apparatus

FIG. 6 is a block diagram showing a control system of the culture apparatus 10.

As shown in FIG. 6, the culture apparatus 10 has a mixed gas supply apparatus 50 supplying a mixed gas containing oxygen to the internal space 106 of the culture bag 100 via the first and second gas supply ports 112, 116. The agitation apparatus 20 also has a motor control apparatus 52 controlling the motors 30, 32, and 34.

The mixed gas supply apparatus 50 includes, for example, a tank (not shown) storing a mixed gas containing oxygen, and a flow regulating valve (not shown) disposed between the tank and the first and second gas supply ports 112, 116.

The mixed gas supply apparatus 50 may be in any form as long as the supply amount can be controlled when the mixed gas is supplied to the internal space 106 of the culture bag 100.

The motor control apparatus 52 of the agitation apparatus 20 can supply electric power to the motors 30, 32, and 34, for example, and is made up of a control board on which a memory and a CPU are mounted. As shown in FIG. 1, the motor control apparatus 52 is configured to change the posture of the stage 28 by controlling the rotation angles θx, θy, and θz of the respective motors 30, 32, and 34. In other words, the motor control apparatus 52 controls the tilt of the stage 28. Specifically, the rotation angles θx, θy, and θz of the respective motors 30, 32, and 34 are controlled such that the culture solution in the internal space 106 of the culture bag 100 is stirred.

Figure 7:
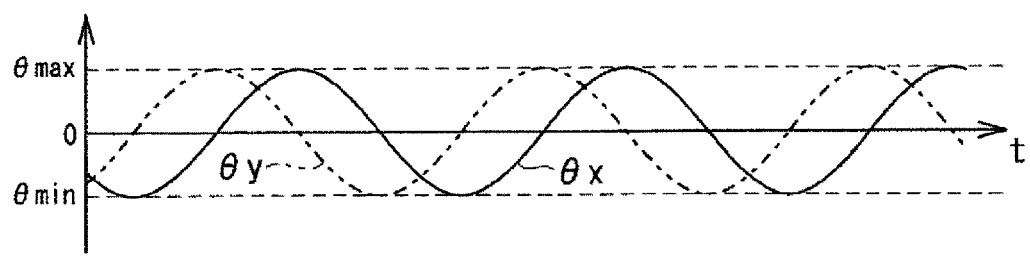
FIG. 7 is a diagram showing a control for agitating a culture solution.

FIG. 7 shows the control of the motors 30, 32, and 34 of the agitation apparatus 20 for agitating the culture solution in the internal space 106 of the culture bag 100.

As shown in FIG. 7, the rotation angle θx of the motor 30 about the first bag axis Xb is controlled at a predetermined frequency (first frequency). The rotation angle θy of the motor 32 about the second bag axis Yb is controlled at a predetermined frequency (second frequency). In the motor control shown in FIG. 7, the motor 34 is stopped. Therefore, the rotation angle θz of the motor 34 about the third bag axis Zb is maintained at zero. When θx is zero, the second bag axis Yb is horizontal, and when θy is zero, the first bag axis Xb is horizontal.

As shown in FIG. 7, the frequency of the rotation angle θx and the frequency of the rotation angle θy are the same in wavelength and amplitude. The rotation angles θx, θy change between a predetermined maximum value (upper limit rotation angle) θ max and a predetermined minimum value (lower limit rotation angle) θ min. In the case of this embodiment, θ max and θ min have the same magnitude (have the absolute value).

As shown in FIG. 7, the frequency of the rotation angle θx and the frequency of the rotation angle θy differ in phase by a quarter wavelength.

Figure 8:
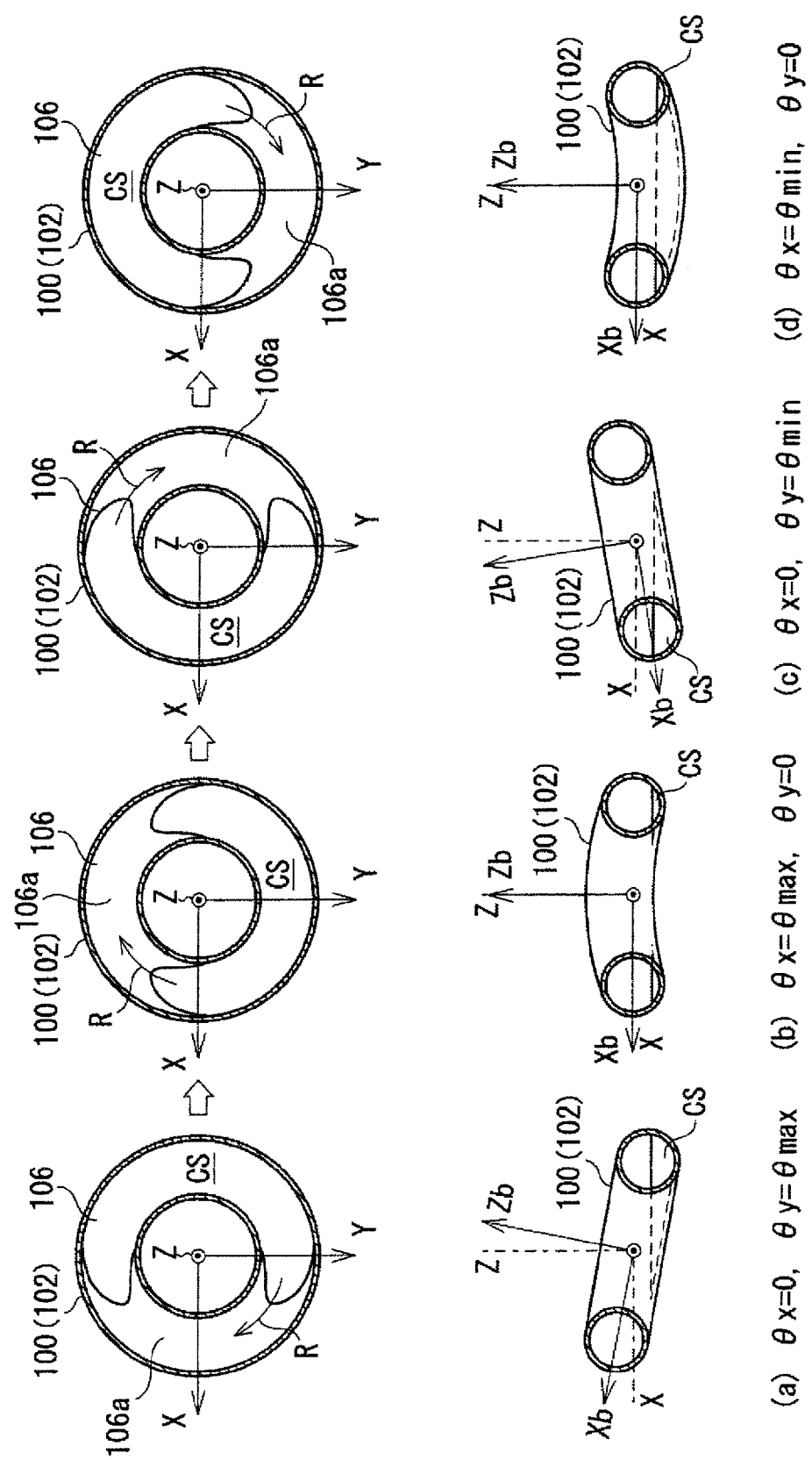
FIG. 8 is top and cross-sectional views of a culture space showing a state of agitating of the culture solution.

FIG. 8 shows top and cross-sectional views of the internal space 106 of the culture bag 100 showing how the culture solution is stirred by the control shown in FIG. 7. The cross-sectional views show a cross section along a Z-X plane.

As shown in FIG. 8, a tilt direction of the culture bag 100 is periodically changed by the motor control shown in FIG. 7. Specifically, a lowest portion in the internal space 106 of the culture bag 100 transitions in the circulating direction R. Consequently, a culture solution CS circulates in the annular internal space 106 of the culture bag 100 (flows in the circulating direction R).

Since the culture solution CS circulates, i.e., the culture solution CS continuously flows along an inner wall surface of the internal space 106 of the culture bag 100, damage to cells suspended in the culture solution CS is suppressed (as compared to when the culture solution CS reciprocates in one direction).

Specifically, since the culture solution CS circulates rather than reciprocates, the culture solution CS is prevented from strongly colliding with the inner wall surface. As a result, a local flow with large shear stress is prevented from occurring due to the collision, and the cells are prevented from being damaged due to a large shear force. Additionally, air bubbles are prevented from being generated due to the strong collision of the culture solution CS with the inner wall surface, and consequently, the cells are prevented from being damaged due to impact caused by burst of the air bubbles.

Due to the motor control shown in FIG. 7, as shown in FIG. 8, a bottom surface 106a of the internal space 106 of the culture bag 100 is partially revealed as the culture solution CS circulates, and the revealed portion transitions in the circulating direction R. Therefore, the culture solution CS gathers together and moves in the internal space 106 in the circulating direction R without being continuous in the circulating direction R.

The "revealment of the bottom surface" as used herein means that at least a portion of the bottom surface appears from the culture solution to such an extent that a liquid film of the culture solution is formed on at least a portion of the bottom surface. For example, this means that the culture solution adheres to the bottom surface to such an extent that the culture solution does not run down even if the bottom surface is tilted. In this description, the "revealment of the bottom surface" is used as a phrase different from "exposure of the bottom surface", which means that no culture solution is present on the bottom surface. In other words, in the case of this embodiment, a revealed portion corresponds to a portion of the bottom surface present at a higher position than the liquid surface of the culture solution in the horizontal state.

The "bottom surface" as used herein refers to a lower portion of an inner surface of the culture vessel coming into contact with the culture solution when the culture vessel is horizontal, i.e., a portion away from the liquid surface of the culture solution.

If the cross section of the internal space of the culture vessel orthogonal to the circulating direction of the culture solution is circular as in the culture bag of the first embodiment, for example, the "bottom surface" is the lower half of the inner surface when the culture vessel is horizontal. Preferably, when the internal space of the culture vessel is viewed in the circulating direction of the culture solution, the "bottom surface" is a portion of the inner surface in an angle range of 120 degrees to 240 degrees when a top portion is at 0 degrees. More preferably, the "bottom surface" is a portion of the inner surface in an angle range of 135 degrees to 225 degrees.

The maximum value θ max and the minimum value θ min of the rotation angles θx, θy of the motors 30, 32 are set such that a portion of the bottom surface 106a of the internal space 106 of the culture bag 100 is revealed due to the circulation of the culture solution CS. Therefore, θ max and θ min are set such that the culture bag 100 is tilted to reveal a portion of the bottom surface 106a.

The reason for revealing a portion of the bottom surface 106a of the internal space 106 of the culture bag 100 in this way, i.e., for forming a liquid film of the culture solution CS, is to dissolve oxygen sufficiently and entirely in the culture solution CS. This is because a gas such as oxygen is dissolved in the culture solution through the liquid surface and therefore spreads in a sufficient amount near the liquid surface without spreading in a sufficient amount in a deep portion away from the liquid surface. Specifically, the reason is to maintain a state, in which an amount of dissolved oxygen (per unit time) in the culture solution CS is larger than oxygen consumption (per unit time) of the cultured cells in the culture solution CS, over the whole culture solution CS in the culture bag 100, preferably, while maintaining an equilibrium state at a partial pressure of oxygen in the gas phase (non-dissolved oxygen outside the culture solution CS) in the culture bag 100.

Figure 9:
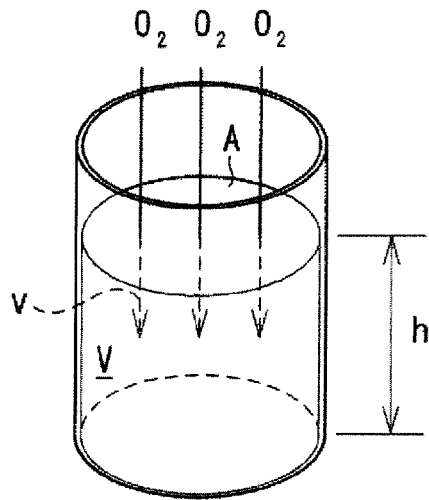
FIG. 9 is a diagram for explaining a two film theory.

Specifically, the dissolution of oxygen into the culture solution CS occurs in the liquid surface of the culture solution CS. In this case, an amount of oxygen dissolved into the culture solution CS per unit time (oxygen transfer rate OTR) is larger at a smaller depth of the culture solution CS. This is based on a two film theory. The two film theory will be described with reference to FIG. 9.

According to the two film theory, an oxygen transfer rate v is a transfer amount of oxygen per unit time from the gas phase to the liquid phase and is defined as Eq. 1:

[Mathematical 1]

$$v = k_L a(C^* - C) \quad \text{(Eq. 1)}$$

where $k_L$ is an oxygen transfer coefficient (m·s$^{-1}$), and a is a gas-liquid contact area (m$^{-1}$) per unit volume. Additionally, kLa is referred to as an oxygen transfer volumetric coefficient. $C^*$ is a saturated oxygen concentration (mol·m$^{-3}$) in the liquid, and C is a dissolved oxygen concentration (mol·m$^{-3}$) in the liquid. The oxygen transfer volumetric coefficient kLa is defined as in Eq. 2:

[Mathematical 2]

$$k_L a = k_L \frac{A}{V} = k_L \frac{1}{h} \quad \text{(Eq. 2)}$$

where A is a gas-liquid contact area (m$^2$), V is a liquid volume (m$^3$), and h is a liquid depth (m).

Referring to Eqs. 1 and 2, the oxygen transfer rate from the gas phase to the liquid phase becomes higher when the room for dissolution of oxygen is larger and becomes higher when the liquid depth is smaller.

Figure 10A:
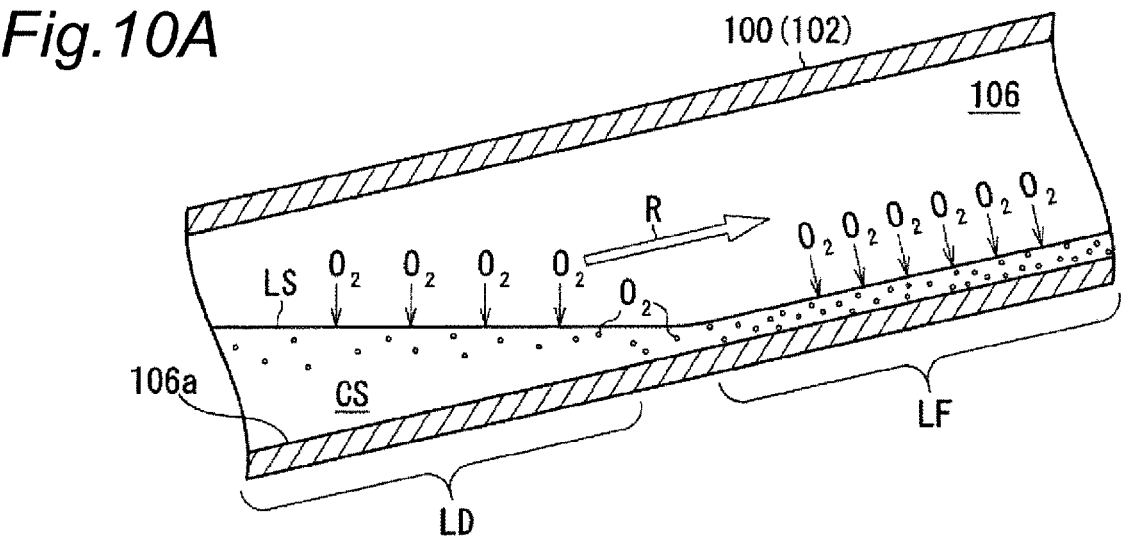
FIGS. 10(*a*) and 10(*b*) are diagrams for explaining dissolution of oxygen in the culture solution.

Applying to this embodiment, oxygen is more quickly dissolved in the culture solution CS when the depth of the culture solution CS is shallower. Therefore, as shown in FIG. 10(a), in a liquid film portion LF of the culture solution CS on the revealed portion of the bottom surface 106a of the internal space 106 of the culture bag 100, oxygen can more quickly be dissolved (per unit time and per unit liquid surface area) than a depth portion LD of the remaining culture solution that is not the liquid film (a portion having a depth larger than the thickness of the liquid film).

Figure 10B:
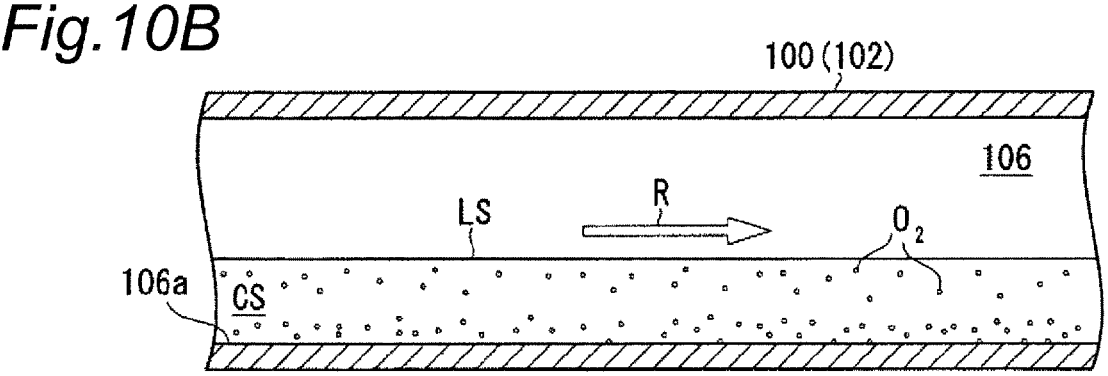

As the bottom surface 106a of the internal space 106 of the culture bag 100 becomes horizontal, the culture solution CS sweeps the revealed portion of the bottom surface 106a. In other words, the liquid film portion LF of the culture solution CS in the revealed portion is absorbed by the depth portion LD of the culture solution CS. Subsequently, when the bottom surface 106a becomes horizontal as shown in FIG. 10(b), the depth of the culture solution CS becomes uniform, and the dissolved oxygen dissolved in the liquid film portion LF is distributed to a deep portion (a portion near the bottom surface 106a) of the culture solution CS. As a result, the dissolved oxygen spreads over from the liquid surface LS of the culture solution CL to the deep portion. Consequently, a sufficient amount of oxygen can be supplied to each of the cells suspended in the culture solution CL while the culture solution CS is stirred.

The culture apparatus 10 as described above can dissolve oxygen necessary for the cells sufficiently and entirely in the culture solution CS while agitating the culture solution CS necessary for the cells. Therefore, a sparger is no longer necessary for dissolving oxygen in the culture solution CS. Additionally, it is not required to stir the culture solution CS more than necessary, i.e., to tilt the culture bag 100 more than the tilt necessary for agitating, so as to dissolve oxygen in the culture solution.

If carbon dioxide is supplied into the culture bag 100 for pH adjustment of the culture solution CS necessary for culture, carbon dioxide dissolves in the culture solution CS as with oxygen.

In the case of the first embodiment, the amount of dissolved oxygen in the culture solution CS can be adjusted in accordance with a change in the oxygen consumption of the cells. Therefore, the apparent oxygen transfer rate of the whole culture solution CS can be adjusted.

For example, if the oxygen consumption of the cells increases and the amount of dissolved oxygen in the culture solution CS decreases, the tilt angle of the culture bag 100 relative to the horizontal direction can be made larger, i.e., the area of the revealed portion can be expanded to a larger area on the bottom surface 106a of the internal space 106 of the culture bag 100, so as to increase the amount of oxygen transferred from the outside of the culture solution into the culture solution (the liquid film portion LF in the revealed portion). As a result, the amount of dissolved oxygen is increased in the culture solution CS. However, this does not mean that the amount of dissolved oxygen can be increased without limit. According to Henry's law, the amount of dissolved oxygen in the culture solution CS is proportional to the partial pressure of oxygen in the gas phase in the culture bag 100 (non-dissolved oxygen outside the culture solution CS). Therefore, when the partial pressure of oxygen is constant, the maximum value of the amount of dissolved oxygen is uniquely determined. Therefore, when the amount of dissolved oxygen in the culture solution CS decreases and is no longer in the equilibrium state, the amount of dissolved oxygen can be increased until returning to the equilibrium state, i.e., until reaching the maximum value corresponding to the partial pressure of oxygen in the gas phase.

In the case of the first embodiment, the area of the revealed portion on the bottom surface 106a of the internal space 106 of the culture bag 100 can be adjusted by adjusting the amplitudes of the rotation angles θx, θy of the motors 30, 32, and the amount of dissolved oxygen can thereby be adjusted.

Additionally, a rate of distribution of dissolved oxygen to the whole culture solution CS can be adjusted.

For example, if the oxygen consumption of the cells rapidly increases and the amount of dissolved oxygen in the culture solution CS rapidly decreases, it is required to increase the amount of dissolved oxygen as described above and then promptly spread the dissolved oxygen over the whole culture solution. In this case, the transition speed of the revealed portion is increased on the bottom surface 106a of the internal space 106 of the culture bag 100, i.e., the sweep speed of the culture solution sweeping the revealed portion is increased. As a result, the dissolved oxygen dissolved in the liquid film portion LF of the culture solution CS in the revealed portion promptly spreads over the whole culture solution.

In the case of the first embodiment, the transition speed of the revealed portion, i.e., the sweep speed of the culture solution sweeping the revealed portion, can be adjusted by adjusting the frequency of the rotation angles θx, θy of the motors 30, 32.

To adjust the area of the revealed portion on the bottom surface 106a of the internal space 106 of the culture bag 100, or to adjust the sweep speed of the culture solution CS sweeping the revealed portion, i.e., to detect a change in the amount of dissolved oxygen in the culture solution CS, the amount (concentration) of dissolved oxygen of the culture solution CS may be measured. The amount of dissolved oxygen in the culture solution CS can be measured by a dissolved oxygen measuring device, for example. When a culture period is long, a dissolved oxygen measuring device to be used is preferably a fluorescent-type measuring device suitable for long-term measurement, rather than a diaphragm-type measuring device requiring regular diaphragm replacement.

The fluorescent-type dissolved oxygen measuring device is configured to measure an amount (concentration) of dissolved oxygen by utilizing a fluorescence phenomenon of molecules. Specifically, a probe of the dissolved oxygen measuring device is disposed in the culture solution. The probe emits ultraviolet light etc., and molecules irradiated with the light (absorbing a light energy) are changed from a ground state to an excited state. Molecules in the excited state emit fluorescence when returning to the ground state. In this case, if oxygen molecules are present nearby, the molecules excited due to absorption of light energy are deprived of energy by the oxygen molecules and are thereby reduced in emission intensity. When the molecular oxygen concentration is higher, the emission intensity becomes lower. By measuring the emission intensity corresponding to the oxygen molecule concentration in an inversely proportional manner, the fluorescent-type dissolved oxygen measuring device measures the amount of dissolved oxygen.

Based on the concentration of dissolved oxygen measured by such a dissolved oxygen measuring device, the culture device 10 (the motor control apparatus 52 thereof) can control at least one of the area of the revealed portion and the transition speed of the revealed portion on the bottom surface 106a of the internal space 106 of the culture bag 100.

Similarly, a pH value of the culture solution CS may be measured by using a pH measuring device so as to control at least one of the area of the revealed portion and the transition speed of the revealed portion on the bottom surface 106a of the internal space 106 of the culture bag 100 based on the measurement result.

For example, as the oxygen consumption of the cells increases, the amount of carbon dioxide discharged from the cells accordingly increases. As a result, the pH of the culture solution decreases so that a culture system may be affected. In this case, by increasing the area of the revealed portion and accelerating the transition speed or by providing either one of the controls, the concentration of carbon dioxide in the culture solution CS can promptly be reduced to a concentration at which equilibrium is achieved at the partial pressure of carbon dioxide in the gas phase (non-dissolved carbon dioxide outside the culture solution CS) in the culture bag 100.

As described above, according to the first embodiment, at the time of culture performed by agitating a culture solution in which cells are suspended, oxygen can sufficiently and entirely be dissolved in the culture solution while suppressing damages to the culture target.

Second Embodiment

A second embodiment is the same as the first embodiment in terms of the principle of dissolving oxygen etc. in a culture solution except that the structures of the culture vessel and the agitation apparatus are different. Therefore, the second embodiment will be described mainly in terms of different points.

Figure 11:
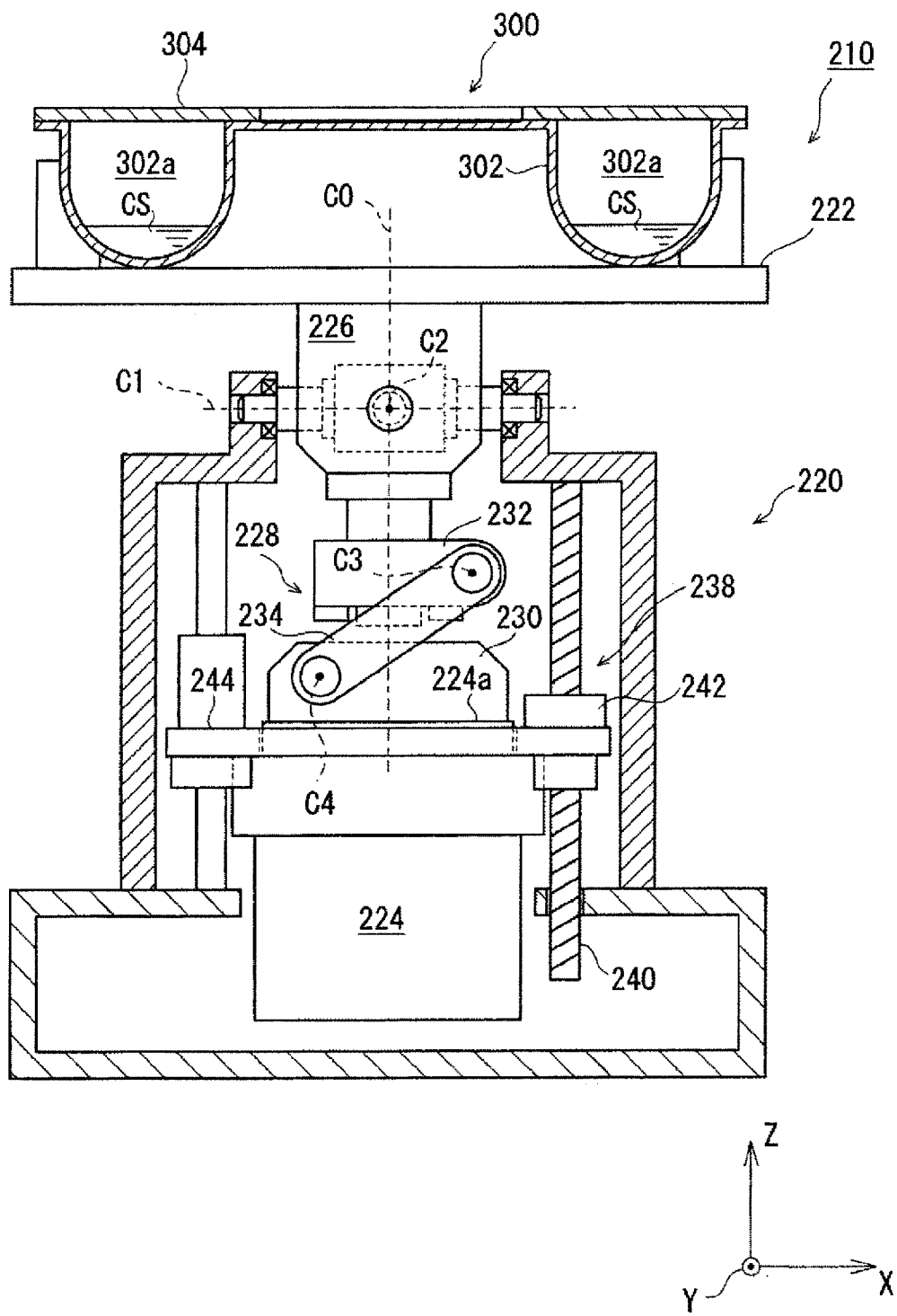
FIG. 11 is a schematic partial cross-sectional view of a culture apparatus according to a second embodiment of the present invention.
Figure 12:
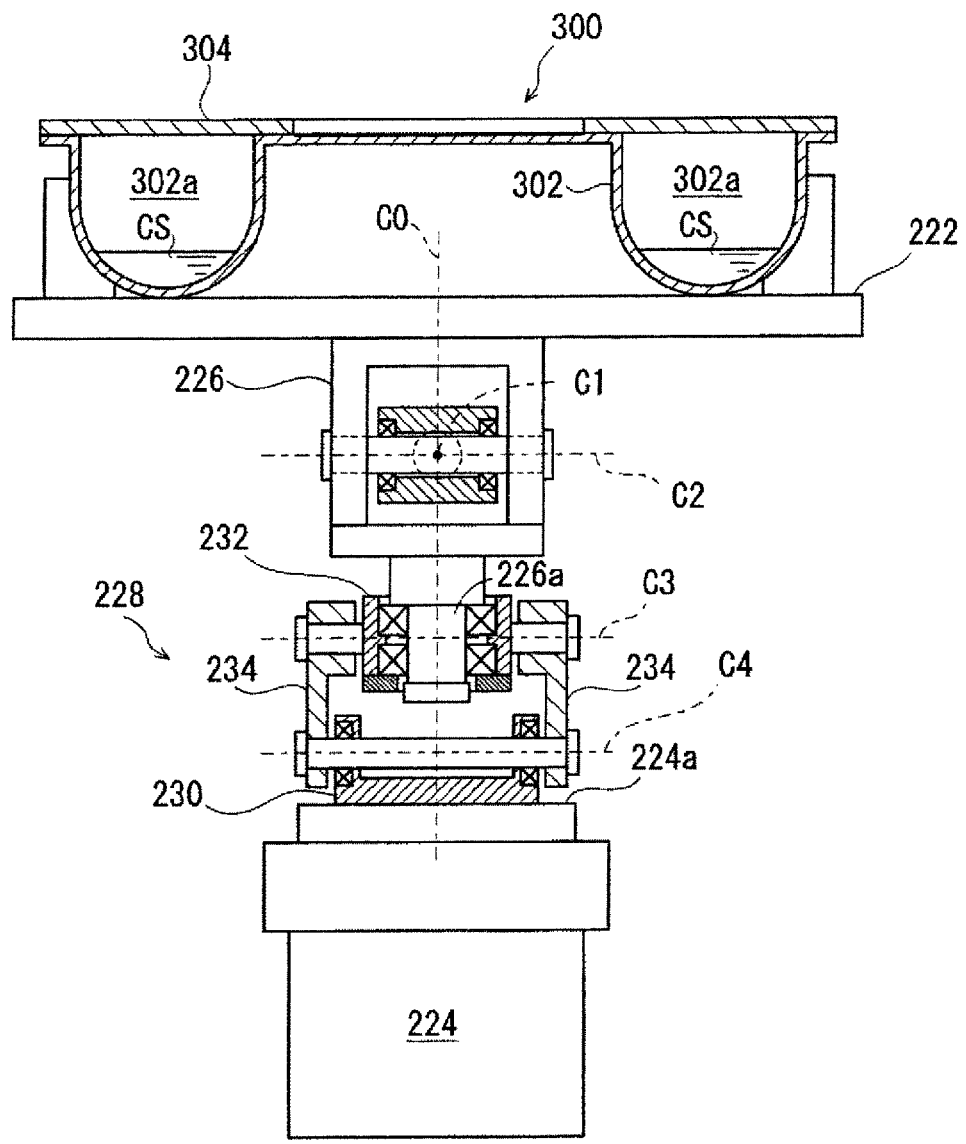
FIG. 12 is a schematic partial cross-sectional view of a portion of the culture apparatus shown in FIG. 11 as viewed in a different direction.
Figure 12:
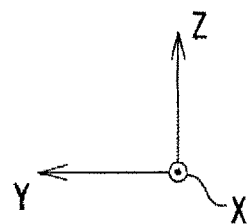

In the case of the second embodiment, as shown in FIGS. 11 and 12, a culture vessel 300 in a culture apparatus 210 includes a main body part 302 including an internal space 302a having an annular recess shape, and a cover part 304 covering the internal space 302a. The main body part 302 is a rigid body and is made of a metal material or an acrylic resin material, for example. The cover member 304 is an annular plate covering the internal space 302a of the main body 302 and includes a port (not shown) such as a gas supply port. The culture solution CS is contained in the internal space 302a of the main body 302, and the culture is performed in the internal space 302a.

An agitation apparatus 220 in the culture apparatus 210 of the second embodiment includes a stage 222 holding the culture vessel 300, and a rotary actuator 224 including a rotating table 224a rotating about a rotation center axis C0 extending in the vertical direction (Z-axis direction).

The stage 222 and the rotary actuator 224 are coupled for driving via a oscillating head 226 and a tilting mechanism 228.

The oscillating head 226 supports the stage 222 and is disposed in the agitation apparatus 220 to be swingable about an axis of oscillation C1 extending in the horizontal direction (Y-axis direction) and an axis of oscillation C2 extending in the horizontal direction (X-axis direction) and orthogonal to the axis of oscillation C1. The oscillating head 226 includes in a lower portion thereof a coupling shaft 226a for coupling for driving via the tilting mechanism 228 to the rotary actuator 224. When the stage 222 is in a horizontal posture, the coupling shaft 226a of the oscillating head 226 extends in the vertical direction (Z-axis direction).

The tilting mechanism 228 is a link mechanism for tilting the stage 222 via the oscillating head 226, i.e., tilting the culture vessel 300 on the stage 222 relative to the horizontal direction. Therefore, the tilting mechanism 228 includes a base part 230, a oscillating head coupling part 232 coupled to the oscillating head 226, and link arms 234 coupling the base part 230 and the oscillating head coupling part 232.

The base part 230 of the tilting mechanism 228 is attached to the rotating table 224a of the rotary actuator 224. Therefore, when the rotary actuator 224 is driven, the base part 230 rotates about the rotation center axis C0 together with the rotating table 224a.

The oscillating head coupling part 232 of the tilting mechanism 228 is slidably disposed around the coupling shaft 226a of the oscillating head 226 via a bearing, for example.

The link arm 234 of the tilting mechanism 228 is configured to couple the base part 230 and the oscillating head coupling part 232. Specifically, the link arm 234 includes one end pivotally fixed to the oscillating head coupling part 232 and the other end pivotally fixed to the base part 230. The rotation axis C3 at one end and the rotation axis C4 at the other end of the link arm 234 extend in the horizontal direction and are parallel to each other.

The rotary actuator 224 with the base part 230 of the tilting mechanism 228 attached thereto is lifted and lowered in the vertical direction (Z-axis direction) by a ball screw mechanism 238.

The ball screw mechanism 238 includes a screw shaft 240 extending in the vertical direction (Z-axis direction), a nut 242 engaged with the screw shaft 240, and a motor (not shown) rotating the screw shaft 240. The nut 242 is attached to a lifting/lowering bracket 244. The rotary actuator 224 is attached to the lifting/lowering bracket 244.

Figure 13:
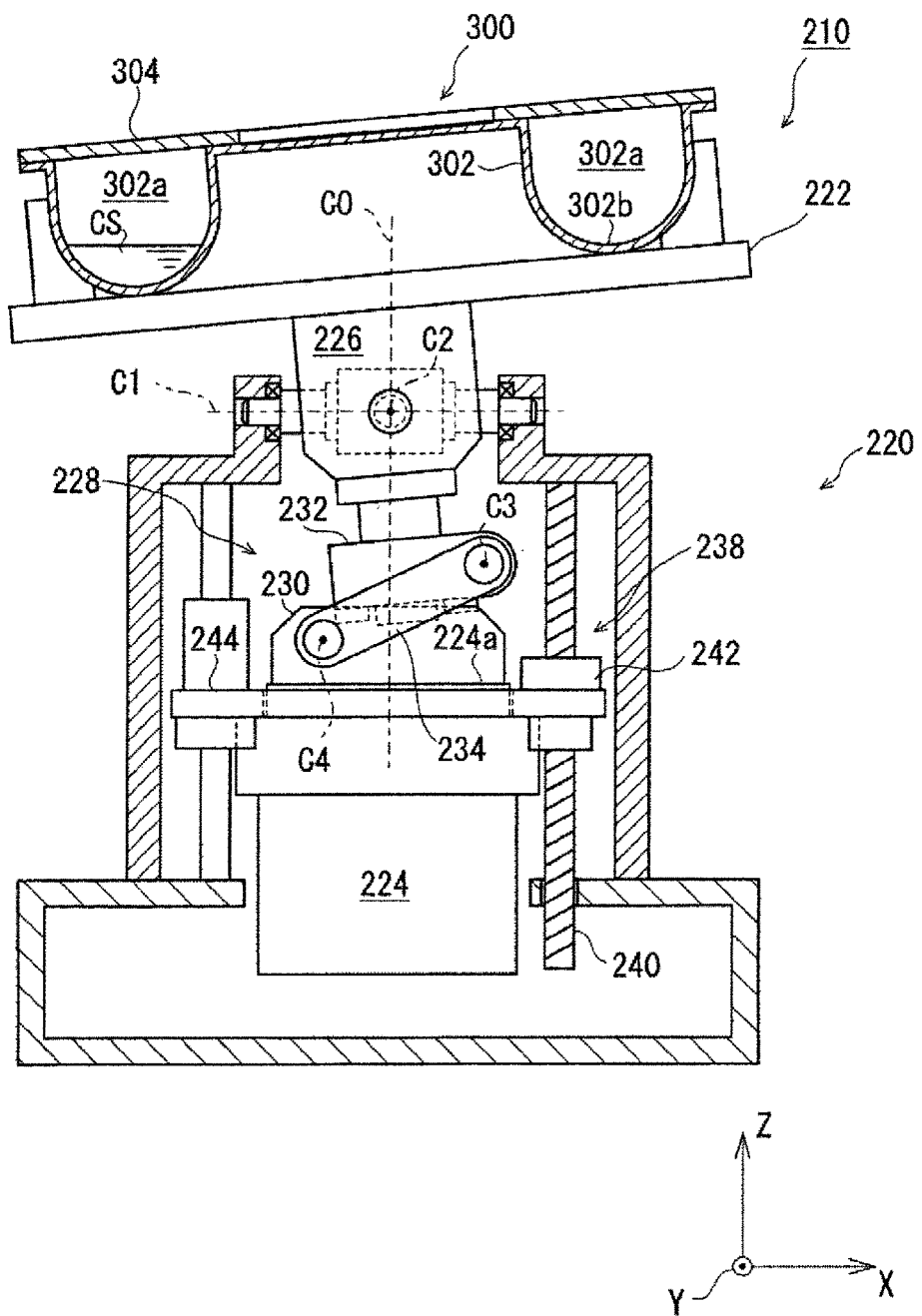
FIG. 13 is a schematic partial cross-sectional view of the culture apparatus shown in FIG. 11 with a culture vessel tilted.

When the ball screw mechanism 238 is driven, the rotary actuator 224 is lifted and lowered together with the lifting/lowering bracket 244 via the nut 242. For example, as shown in FIG. 13, when the rotary actuator 224 is lifted by the ball screw mechanism 238, the stage 222 is tilted via the tilting mechanism 228. Specifically, the base part 230 of the tilting mechanism 228 attached to the rotary actuator 224 is lifted, which causes the link arms 234 to push the oscillating head coupling part 232. As a result, the oscillating head 226 rotate together with the oscillating head coupling part 232 about at least one of the swinging axes C1, C2 (the axis of oscillation C2 in FIG. 13). As a result, the stage 222 tilts, and a bottom surface 302b of the internal space 302a of the culture vessel 300 held by the stage 222 is partially revealed.

As shown in FIG. 13, when the rotary actuator 224 is driven to rotate the rotating table 224a while the stage 222 is tilted such that the bottom surface 302b is partially revealed, the tilting mechanism 228 rotates about the rotation axis C0, so that the tilt direction of the stage 222 changes. As a result, the culture solution CS circulates, and the revealed portion transitions on the bottom surface 302b of the internal space 302a of the culture vessel 300.

In the case of the second embodiment, the revealed portion on the bottom surface 302b of the internal space 302a of the culture vessel 300 transitions (circulates) due to the rotation of the one rotary actuator 224. On the other hand, in the case of the first embodiment described above, the revealed portion on the bottom surface 106a of the internal space 106 of the culture bag 100 circulates due to the synchronous rotation of the two motors 30, 32. In the case of the second embodiment, only the one rotary actuator 224 needs to be controlled, the configuration and control details of the control system can be simplified as compared to the first embodiment in which the two motors 30, 32 are synchronously controlled.

In the case of the second embodiment, a dissolved oxygen measuring device and a pH measuring device may be disposed so as to adjust the amount of dissolved oxygen in the culture solution CS and the pH value of the culture solution CS as in the first embodiment described above. Based on the measurement results of the dissolved oxygen measuring device and the pH measuring device, the culture apparatus 210 controls at least one of the area of the revealed portion and the transition speed of the revealed portion on the bottom surface 302b of the internal space 302a of the culture bag container 300.

In the case of the second embodiment, the tilt of the culture vessel 300, i.e., the area of the revealed portion on the bottom surface 302b of the internal space 302a, can be adjusted by adjusting the height position (position in the Z-axis direction) of the rotary actuator 224 with the ball screw mechanism 238. In the case of the second embodiment, the transition speed of the revealed portion can be adjusted by adjusting the rotation speed of the rotary actuator 224.

As described above, according to the second embodiment, as in the first embodiment described above, at the time of culture performed by agitating a culture solution in which cells are suspended, oxygen can sufficiently and entirely be dissolved in the culture solution while suppressing damages to the culture target.

Although the present invention has been described with the first and second embodiments, the embodiments of the present invention are not limited to thereto.

For example, in the case of the first embodiment described above, the culture target is suspended cells; however, the culture target may be adherent cells. In the case of adherent cells, the adherent cells are allowed to adhere to microcarriers so that the adherent cells are acclimated to floating.

Furthermore, in the case of the first and second embodiments described above, the internal spaces of the culture vessels 100, 300 for performing the culture are annular; however, the embodiments of the present invention are not limited thereto. The internal space of the culture vessel is not limited to an annular shape as long as the culture solution can at least circulate. However, an inner circumferential surface of the internal space of the culture vessel is preferably a curved surface without a corner, i.e., a continuous curved surface, so that the culture solution can smoothly circulate without collision.

Furthermore, in the case of the first embodiment, as shown in FIG. 1, the agitation apparatus 20 changes the posture of the culture bag 100 by swinging about the first bag axis Xb and the second bag axis Yb extending in the horizontal direction and orthogonal to each other. In the case of the second embodiment, as shown in FIG. 11, the posture of the culture vessel 300 is changed by swinging about the swinging axes C1, C2 of the oscillating head 226. Therefore, in the case of the first and second embodiments described above, the culture vessel is tilted relative to the horizontal direction to partially reveal the bottom surface of the internal space, and the tilt direction of the culture vessel is changed so that the revealed portion transitions in the circulating direction. However, the embodiments according to the present invention are not limited thereto. The culture vessel may be changed in not only posture but also position as long as at least the culture solution circulates in the internal space of the culture vessel so that the bottom surface of the internal space of the culture vessel is partially revealed and that the revealed portion transitions in the circulating direction.

Additionally, in the case of the first embodiment described above, the internal space of the culture vessel orthogonal to the circulating direction of the culture solution has a circular cross section and the bottom surface that is a curved surface; however, the bottom surface of the culture vessel may be a flat surface. In this case, the cross-sectional shape of the internal space is square or rectangular, for example. To dissolve more oxygen in the culture solution, a bottom surface of the solution is preferably as large as possible.

Although the first and second embodiments described above have been described in terms of dissolution of oxygen into the culture solution, the gas dissolved into the culture solution according to the embodiments of the present invention is not limited to oxygen. For example, a single gas or a mixed gas necessary for culture, such as only a carbon dioxide gas or a mixed gas of oxygen and carbon dioxide, may be dissolved into the culture solution.

Therefore, in a broad sense, the culture apparatus according to the embodiments of the present invention is an apparatus including a culture vessel including an internal space containing a culture solution in which a culture target is suspended, a gas supply apparatus supplying a single gas or a mixed gas to the internal space of the culture vessel, and an agitation apparatus agitating the culture solution by changing position and posture of the culture vessel, and the agitation apparatus changes the position and posture of the culture vessel to circulate the culture solution in the internal space of the culture vessel so that a bottom surface of the internal space of the culture vessel is partially revealed and that the revealed portion transitions in a circulating direction.

In a broad sense, a culture method according to the embodiments of the present invention is a culture method including supplying a single gas or a mixed gas to an internal space of a culture vessel containing a culture solution, and agitating the culture solution by changing position and posture of the culture vessel to circulate the culture solution in the culture vessel so that a bottom surface of the internal space of the culture vessel is partially revealed and that the revealed portion transitions in a circulating direction.

The present invention is applicable to culture performed with agitating of a culture solution.

What is claimed is:

1. A culture apparatus comprising:
a culture vessel including an internal space containing a culture solution in which a culture target is suspended;
a gas supply apparatus configured to supply a single gas or a mixed gas to the internal space of the culture vessel; and
an agitation apparatus configured to agitate the culture solution by changing position and posture of the culture vessel,
wherein the agitation apparatus is configured to change the position and posture of the culture vessel to circulate the culture solution in the internal space of the culture vessel so that a bottom surface of the internal space of the culture vessel is partially revealed and that the revealed portion transitions in a circulating direction, and
wherein the agitation apparatus comprises:
a stage holding the culture vessel,
a single rotary actuator including a rotating table rotating about a rotation center axis extending in a vertical direction,
an oscillating head configured to support the stage swingably about a first axis of oscillation extending in a horizontal direction and a second axis of oscillation extending in a horizontal direction and orthogonal to the first axis of oscillation and that includes a coupling shaft,
a tilting mechanism disposed on the rotating table of the single rotary actuator and including an oscillating head coupling part slidably disposed around the coupling shaft of the oscillating head, a base part attached to the rotating table of the single rotary actuator, and
no more than two link arms, each link arm including one end pivotally fixed to the oscillating head coupling part and the other end pivotally fixed to the base part, and
a rotary actuator lifting/lowering mechanism configured to:
lift and lower the single rotary actuator in the vertical direction such that the base part of the tilting mechanism attached the rotating table of the single rotary actuator is, respectively, lifted towards and lowered away from the oscillating head,
draw the base part towards the oscillating head by lifting the single rotary actuator such that the other end of each of the no more than two link arms approaches the oscillating head coupling part while the one end of each of the no more than two link arms pushes the oscillating head coupling part, so as to tilt the oscillating head about at least one of the first axis or the second axis through the coupling shaft around which the oscillating head coupling part is slidably disposed, and
adjust a height position of the single rotary actuator to adjust an area of the revealed portion on the bottom surface of the internal space of the culture vessel.

2. The culture apparatus according to claim 1, wherein the agitation apparatus is configured to tilt change the position and posture of the culture vessel by tilting the culture vessel relative to a horizontal direction so that the bottom surface of the internal space of the culture vessel is partially revealed and to change a tilt direction of the culture vessel so that the revealed portion transitions in the circulating direction.

3. The culture apparatus according to claim 2, wherein the agitation apparatus includes:
a stage holding the culture vessel,
a first motor swinging the stage at a first frequency about a first axis of oscillation extending in a horizontal direction, and
a second motor swinging the stage at a second frequency about a second axis of oscillation extending in a horizontal direction and orthogonal to the first axis of oscillation, and
wherein the first frequency and the second frequency are the same in wavelength and amplitude and different in phase by a quarter wavelength.

4. The culture apparatus according to claim 2, further comprising:
a dissolved oxygen measuring device configured to measure a concentration of dissolved oxygen in the culture solution,
wherein the culture apparatus controls at least one of an area of the revealed portion on the bottom surface of the internal space of the culture vessel and a transition speed of the revealed portion based on the measured concentration of dissolved oxygen.

5. The culture apparatus according to claim 2, further comprising:
a pH measuring device configured to measure a pH value of the culture solution,
wherein the culture apparatus controls at least one of the area of the revealed portion on the bottom surface of the internal space of the culture vessel and the transition speed of the revealed portion based on the measured pH value.

6. The culture apparatus according to claim 1, wherein the internal space of the culture vessel is annular.

7. The culture apparatus according to claim 1, wherein the culture vessel is a flexible culture bag.

8. The culture apparatus according to claim 1, wherein the culture target is suspended cells or adherent cells acclimated to floating.

* * * * *